(12) United States Patent
Kramer et al.

(10) Patent No.: US 7,049,080 B2
(45) Date of Patent: May 23, 2006

(54) PROCESS FOR DETECTING SERINE/THREONINE KINASE ACTIVITY

(76) Inventors: Joachim Kramer, c/o EVOTEC BioSystems AG Schnackenburgallee 114, Hamburg (DE) D-22525; Thomas Mander, c/o EVOTEC BioSystems AG Schnackenburgallee 114, Hamburg (DE) D-22525; Richard Bethell, c/o Pfizer Limited, Sandwich, Kent (GB) CT13 9NJ; Neil Benson, c/o Pfizer Limited, Sandwich, Kent (GB) CT13 9NJ; Helen Boyd, c/o Pfizer Limited, Sandwich, Kent (GB) CT13 9NJ; Pam Greengrass, c/o Pfizer Limited, Sandwich, Kent (GB) CT13 9NJ; Ross Kinloch, c/o Pfizer Limited, Kent (GB) CT13 9NJ ( * ) Notice: Subject to any disclaimer, the term of this patent is extended or adjusted under 35 U.S.C. 154(b) by 236 days.

(21) Appl. No.: 09/923,716

(22) Filed: Aug. 7, 2001

(65) Prior Publication Data
US 2002/0086336 A1    Jul. 4, 2002

Related U.S. Application Data

(60) Provisional application No. 60/224,331, filed on Aug. 11, 2000.

(51) Int. Cl.
G01N 33/53     (2006.01)
(52) U.S. Cl. ............ 435/7.1; 435/7.93; 435/7.94; 435/7.95; 435/194; 436/501
(58) Field of Classification Search ............ 435/7.1, 435/7.92, 68.1, 69.2, 194, 7.93, 7.94, 7.95; 436/501, 164
See application file for complete search history.

(56) References Cited

U.S. PATENT DOCUMENTS

2003/0023990 A1 * 1/2003 Davis et al. ............ 800/8
2003/0027236 A1 * 2/2003 Burke et al. ............ 435/15

FOREIGN PATENT DOCUMENTS

WO    WO 96/3642    * 11/1996
WO    9929894    6/1999

OTHER PUBLICATIONS

Mosier et al., Immunoassay Protocol for Quantitation of Protein Kinase Activities, Methods in Enzymology, vol. 305, May 2000, pp. 410-416.*
Lawler et al., "Synergistic activation of SAPK1/JNK1 by two MAP kinase kinases *in vitro*", Current Biology, vol. 8, 25.
Khokhlatchev, "Reconstitution of Mitogen-activated Protein Kinase Phosphorylation Cascades in Bacteria", The Journal of Biological Chemistry, vol. 272, No.17.
Borgne et al., "Sequential Dephosphorylation of p. 34$^{cdc2}$ on Thr-14 and Tyr-15 at the Prophase/Metaphase Transition", The Journal of Biological Chemistry, vol. 271, No. 44.
Seethala, "A Fluorescense Polarization Competition Immunoassay for Tyrosine Kinases", Analytical Biochemistry 255, 1998.
Fleming et al., "Synergistic activation of stress-activated protein kinase 1/c-Jun N-terminal kinase (SAPK1/JNK) isoforms by mitogen-activated protein kinase kinase 4 (MKK4) and MKK7", Biochem. J. (2000) 352.
Wu et al., "Identificate of a High-Affinity Anti-Phosphoserine Antibody for the Development of a Homogeneous Flueorescence Polarization Assay of Protein Kinase C", Jounral of Biomolecular Screening vol. 5, No. 1, 2000.
Khokhlatchev Andrei et al., "Reconstitution of Mitogen-Activated Protein Kinase Phosphorylation Cascades in Bacteria: Efficient Synthesis of Active Protein Kinase", *Journal of Biological Chemistry*, vol. 272, No. 17, 1997, pp. 11057-11062.
Martin Humberto et al., "Regulatory Mechanisms for Modulation of Signaling Through the Cell Integrity S1t2-mediated Pathway in *Saccharomyces cerevisiae*", *Journal of Biological Chemistry*, vol. 275, No. 2, Jan. 14, 2000 pp. 1511-1519.
Seethala Ramakrishina et al., "A Flurescence Polarization Competition Immunoassay for Tyrosine Kinases", *Analytical Biochemistry*, Academic Press, San Diego, CA., vol. 255, Jan. 15, 1998, pp. 257-262.
Wu Jinzi J. et al., "Identification of a High-Affinity Anti-Phosphoserine Antibody for the Development of a Homogeneous Fluorescence Polarization Assay of Protein Kinase C.", *Journal of Biomolecular Screening*, vol. 5, No. 1, Feb. 2000, pp. 23-30.
Lawler Sean et al., "Synergistic Activation of SAPK1/NJK1 by TWo MAP Kinase Kinases in Vitro", *Current Biolog* vol. 8, No. 25, Dec. 17, 1998, pp. 1387-1390.
Hoffmann Ralf et al.; "Phosphorylation of the C-Terminal Sites of Human p53 Reduces Non-Sequence-Specific DNA Binding as Modeled with Synthetic Peptides", *Biochemistry*, vol. 37, No. 39, pp. 13755-13764.
Barancik Miroslav et al., "Okadaic Acid and Anisomycin are Protective and Stimulate the SAPK/JNK Pathway", *Journal of Cardiovascular Pharmacology*, vol. 34, No. 2, Aug. 1999, pp. 182-190.
Fleming Yvonne et al., "Synergistic Activation of Stress-Activated Protein Kinase 1/c-June N-Terminal Kinase (SAPK1/JNK) Isoforms by Mitogen-Activated Protein Kinase Kinase 4 (MKK4) and MKK7", *Biochemical Journal*, vol. 352, No. 1, Nov. 15, 2000, pp. 145-154.

* cited by examiner

*Primary Examiner*—Long V. Le
*Assistant Examiner*—Gary W. Counts
(74) *Attorney, Agent, or Firm*—Baker Botts LLP

(57) ABSTRACT

The present invention describes a process for detecting threonine or serine kinase activity in an immunoassay using a pre-phosphorylated substrate.

24 Claims, 7 Drawing Sheets

PROCESS FOR DETECTING SERINE/THREONINE KINASE ACTIVITY

This application claims the benefit of Provisional application Ser. No. 60/224,331, filed Aug. 11, 2000.

BACKGROUND OF THE INVENTION

The present invention relates to a process for detecting threonine or serine (threonine/serine) kinase activity in an immunoassay. The invention further relates to a kit for carrying out the assay and to a preferably luminescently labelled ligand.

Protein kinases usually catalyse the transfer of the γ-phosphate group from ATP to a serine, threonine or tyrosine residue of an acceptor protein. These enzymes play an important role in signal transduction within cells. Detecting the activity of protein kinases would be useful for the high-throughput screening of chemical libraries. Inhibitors or activators of kinase activity, particularly low-molecular weight compounds, could eventually be developed into drugs used for the treatment of e.g. ischaemic heart disease, liver failure, diabetic neuropathies, stroke, neurodegenerative disorders including Parkinsons disease and Alzheimers disease, inflammatory diseases including asthma, rheumatoid arthritis, inflammatory bowel disease, septic shock and cancer.

It is known that mitogen-activated protein kinases (MAPK) (also referred to as stress activated protein kinases, SAPK) mediate many of the cellular effects of growth factors, cytokines and stress, leading to cell growth, differentiation and oncogenesis. MAPK/SAPK activation requires dual phosphorylation on threonine and tyrosine within the motif threonine-Xaa-tyrosine, where Xaa represents proline in the c-Jun NH2-terminal kinases (JNKs). This activation is catalysed by several MAPK-kinases (e.g. MKK4(SKK1) or MKK7 (SKK4)) which phosphorylate both the threonine and tyrosine residues of the threonine(183)-proline-tyrosine (185) motif within the active site loop of JNK1/2/3. The MKK7 kinase has a high preference for the threonine residue whereas MKK4 preferentially phosphorylates tyrosine. This synergistic activation of JNK1/2/3 is described by Lawler S. et al in Current Biology 8, 1387 to 1390 (1998) and Fleming Y et al. (Biochemical Journal, 352, 145–154, 2000). Up to now the identification of an appropriate substrate which could be used to screen for specific MKK7 inhibitors is complicated by the fact that there are no synthetic substrate peptides described in the literature. The situation becomes even more critical in homogeneous assays as a potential MKK7 substrate peptide should have both a reasonable Km for MKK7 and a high affinity for the phospho-threonine specific detection antibody in parallel. Although generic anti-phospho-tyrosine antibodies with high affinity and specificity are available for tyrosine-directed kinases (e.g. p60c-src kinase), attempts to develop generic anti-phospho-threonine/anti-phospho-serine antibodies for the same purpose have been to date less successful.

Antibodies which bind to phosphorylated threonine or serine residues with high affinity only recognize the phosphorylated amino acid in the context of the surrounding peptide sequence. For antibodies binding to JNK1/2/3 or peptide derivatives thereof, recognition is therefore dependent on two criteria: 1) MKK7-dependent phosphorylation of threonine and 2) phosphorylation of the tyrosine amino acid residue. If one of the two criteria is not fulfilled, an antibody raised against fully activated JNK1/2/3 will not specifically detect the phosphorylation site.

In Anal. Biochem. 255, 257 to 262 (1998) a fluorescence polarization (FP) competition immunoassay for tyrosine kinases using an appropriate substrate for this kinase is described. The kinase reaction was performed by incubation of the peptide substrate with ATP and lymphoid T-cell protein tyrosine kinase followed by termination of the reaction with EDTA plus a fluorescein-phosphopeptide. Following the addition of an anti-phosphotyrosine antibody, the fluorescence polarization signal was measured. The phosphorylated product formed in the assay competes with the fluorescein-phosphopeptide for binding to the anti-phosphotyrosine antibody. The kinase activity results in a reduction of the FP signal and the FP signal is therefore inversely proportional to the phosphorylated product formed in the reaction.

However, such an approach for a generic assay principle for serine/threonine kinases is not realizable to date. This is because there are no anti-phospho-serine/-threonine antibodies available that bind specifically, and with high affinity, to phosphoserine or phosphothreonine residues in the absence of additional specific amino acid sequences adjacent to the phosphorylated amino acid.

SUMMARY OF THE INVENTION

It was therefore the object of the present invention to establish an assay method for detecting serine/threonine kinases or their enzymatic activity. The assay method is highly reliable and simple to perform without the need to develop specific high affinity anti-phospho-serine/-threonine antibodies.

This object has been solved by the assay process according to the features of claim 1.

As used herein, the term "kinase" refers to an enzyme capable of phosphorylating its substrate. A "serine/threonine kinase" refers to an enzyme capable of phosphorylating its substrate at a serine or threonine residue. The term "bis-phosphorylated" or "double phosphorylated" indicates that a protein or peptide comprising the sequence motif -Z-X—Y— or —Y—X-Z- is phosphorylated both at the Z and the Y position. Unless otherwise indicated, the term "bis-phosphorylated" or "double phosphorylated" as used herein does not exclude the possibility that said protein or peptide is further phosphorylated at positions other than Y and Z.

The present invention relates to a process for detecting threonine or serine kinase activity in an immunoassay which comprises the following steps:
a) providing a protein or peptide comprising the sequence motif -Z-X—Y— or —Y—X-Z- wherein
Z=threonine or serine
X=a sequence of preferably between 1 and 1000 amino acids which may be the same or different
Y=tyrosine, threonine or serine as a substrate for threonine or serine kinases, said protein or peptide being pre-phosphorylated at the Y position;
b) incubating the peptide or protein with a phosphate donor and a threonine or serine kinase to form a bis-phosphorylated protein or peptide;
c) adding an antibody having a specificity to the peptide/protein that has been phosphorylated at threonine or serine in the Z position; and d) detecting the threonine or serine kinase activity.

Or to put it in other words, the invention relates to a method for determining the phosphorylating activity of an enzyme which comprises the steps of:
a) combining said enzyme with a protein or peptide comprising the sequence motif -Z-X—Y— or —Y—X-Z- wherein
Z=threonine or serine
X=a sequence of preferably between 1 and 1000 amino acids which may be the same or different
Y=phosphotyrosine, phosphothreonine or phosphoserine,
said protein or peptide capable of being phosphorylated at the Z position by said enzyme;
a phosphate donor; and
an antibody having a specificity to a peptide/protein which is phosphorylated both at the Y and Z position; and b) detecting the enzyme activity.

All assay components might be combined simultaneously or stepwise. The substrate might in particular be combined with said enzyme before the addition of said antibody.

Particularly, the antibody has a specificity to the bis-phosphorylated product of the kinase reaction. By detecting the presence, absence or amount of the product-antibody complex, a threonine or serine kinase activity can be measured. Or to put it in another way: the invention also allows for the determination of the phosphorylation of a substrate molecule by an enzyme at an amino acid selected from the group consisting of serine and threonine.

The present invention also relates to a kit for detecting threonine or serine kinase activity in an immunoassay which comprises the following components:
preferably a threonine or serine kinase;
a pre-phosphorylated substrate as defined above;
an antibody as defined above; and
preferably reaction buffers including a phosphate donor.

The present invention also relates to a labelled, preferably luminescently labelled, ligand for use in a serine/threonine kinase assay comprising the sequence motif -Z-X—Y— or —Y—X-Z- wherein
Z=threonine or serine
X=a sequence of preferably between 1 and 1000 amino acids which may be the same or different
Y=tyrosine, threonine or serine
said protein or peptide ligand being phosphorylated at the Z and Y position.

The subclaims define preferred embodiments of the process of the present invention.

The process of the present invention as well as the kit and the labelled ligand may be used for screening for specific modulators of serine or threonine kinase activity. They are particularly suitable for screening compound libraries in order to locate molecules which inhibit or activate kinases. These molecules may be promising candidates for designing drugs used for the treatment of e.g. ischaemic heart disease, liver failure, diabetic neuropathies, stroke, neurodegenerative disorders including Parkinsons' disease and Alzheimers' disease, inflammatory diseases including asthma, rheumatoid arthritis, inflammatory bowel disease, septic shock and cancer. Screening for an agent capable of increasing or decreasing the phosphorylating activity of the enzyme typically comprises the steps of (i) performing the process as outlined above in the presence and in the absence of said agent; and (ii) comparing the activity of said enzyme in the presence of said agent with the activity of said enzyme in the absence of said agent to determine whether the phosphorylating activity of said enzyme in the presence of said agent is increased or decreased. However, the subject of the present invention might also be useful for the study of the functionality of an enzyme. For instance, one could check whether an unknown protein belongs to the group of serine/threonine kinases or whether a specific serine/threonine kinase is biologically active.

BRIEF DESCRIPTION OF THE DRAWINGS

The accompanying figures illustrate the present invention. Abbreviations are used as follows:
P1°   H-Lys-Phe-Met-Met-Thr-Pro-pTyr-Val-Val-Thr-Arg-NH2 (SEQ ID NO:1)
P1*   H-Lys-Phe-Met-Met-pThr-Pro-Tyr-Val-Val-Thr-Arg-NH2 (SEQ ID NO:2)
P1*°  H-Lys-Phe-Met-Met-pThr-Pro-pTyr-Val-Val-Thr-Arg-NH2 (SEQ ID NO:3)
TAMRA-P1*°5-TAMRA-AEEA-Lys-Phe-Met-Met-pThr-Pro-pTyr-Val-Val-Thr-Arg-NH2 (SEQ ID NO:4)
TAMRA 5'-(6-carboxytetramethylrhodamine)
AEEA 8-amino-3,6-dioxaoctanoic acid linker In the figures the following is shown.

DETAILED DESCRIPTION OF THE INVENTION

Figure 1:
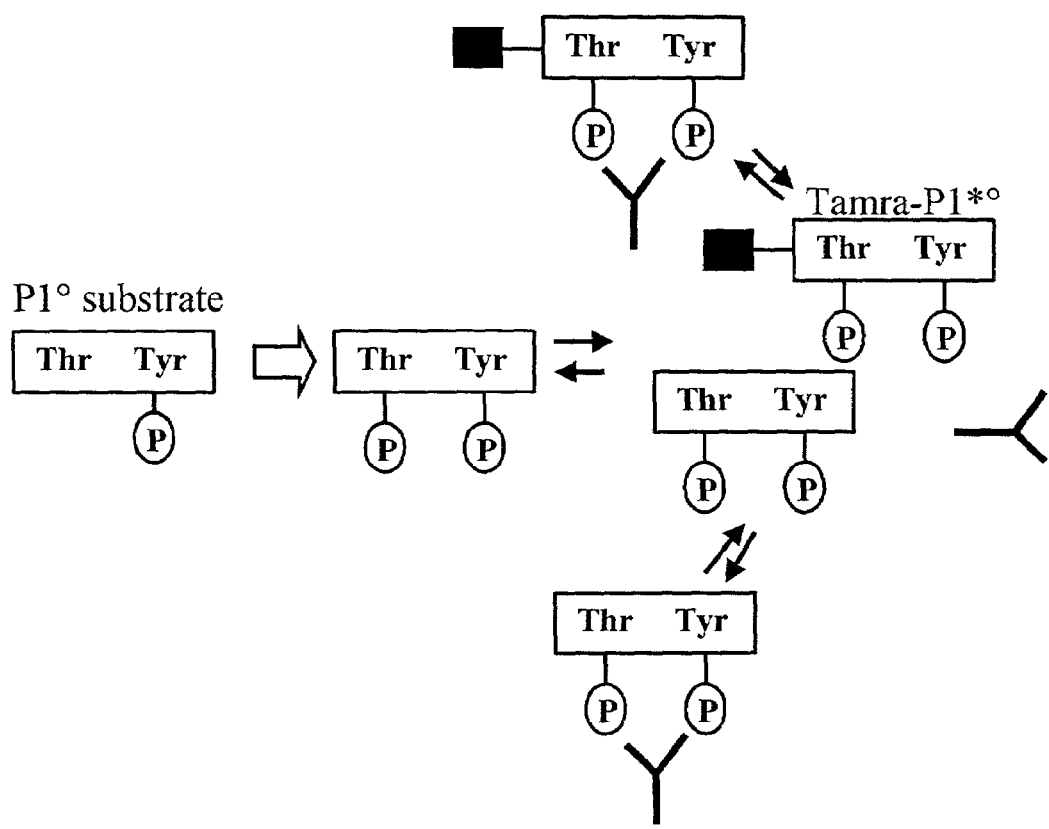
FIG. 1 is a schematic drawing of a preferred embodiment of the assay principle of the present invention.

According to the invention, a protein or peptide comprising the sequence motif -Z-X—Y— or —Y—X-Z-, wherein Z=threonine or serine; X=a sequence of preferably between 1 and 1000 amino acids which may be the same or different; Y=tyrosine, threonine or serine, is used as a substrate for the threonine or serine kinase. According to the present invention said protein or peptide is pre-phosphorylated at the Y position. It has been shown that the proteins and peptides being pre-phosphorylated at the Y residue can be successfully used as synthetic substrates for threonine or serine kinases.

In the sequence motif, any amino acid or sequence of amino acids (X) can be inserted between Z and Y. The number of amino acids is preferably in the range of 1 to 1000 amino acids. A range of 1 to 1000 is preferred to include both linear and conformational antibody epitopes. X is particularly at least one amino acid, any other short amino acid sequences having at least two amino acids, such as oligopeptides, being also included. Preferably, X is proline or glutamate or glycine.

The antibody used is usually a monoclonal or polyclonal antibody.

It has been shown that a particularly preferred antibody is a polyclonal antibody specific for bis-phosphorylated, in particular activated JNK. Such antibodies are commercially available.

It has been revealed that the antibody specifically recognizes a phosphorylated threonine or serine residue at the Z position within both a synthetic substrate peptide or bis-phosphorylated, in particular activated JNK.

The immunoassay according to the present invention is amenable to be carried out in a homogeneous assay format (i.e. "mix, incubate, and read"). This assay format is very advantageous because it is suitable for both high throughput screening (HTS) of potential drugs and secondary assays.

The immunoassay of the present invention may be performed as a direct binding immunoassay, preferably a homogeneous direct binding immunoassay.

In the direct binding immunoassay, a labelled peptide/protein or a labelled antibody is used. The labelling may be carried out according to conventional standard techniques. Preferably, the peptide/protein or antibody is labelled using a luminescent or a radioactive tag or by using specific labelling molecules such as a reporter enzyme or an affinity ligand.

The assay of the present invention may also be performed as a competition immunoassay, preferably a homogeneous indirect binding immunoassay.

In this indirect binding immunoassay, a labelled double-phosphorylated ligand is added to compete with the double-phosphorylated peptide or protein for binding to the antibody. The ligand is preferably labelled using a luminescent or a radioactive tag or by using specific labelling molecules such as a reporter enzyme or an affinity ligand.

In general, fluorescence detection offers a preferred alternative to the use of radiotracers, as fluorescence not only offers detection limits comparable to those of radioactivity but also eliminates the cost of radioactive waste disposal.

In case of using a protein as a substrate containing the above motif, the JNK protein is preferably used, which is the c-Jun N-terminal kinase. JNK kinase is also known in the literature as the stress-activated protein kinase 1 (SAPK1).

When it is more convenient to use a peptide substrate, the peptide sequence is preferably selected from the active-site loop, e.g. for MKK7 from the JNK1/2/3 active site. For instance, said peptide for MKK7 comprises or is composed of the amino acid sequence H-Lys-Phe-Met-Met-Thr-Pro-pTyr-Val-Val-Thr-Arg-NH$_2$, (SEQ ID NO:1) wherein p means phosphorylated.

When the incubation of the protein or peptide is carried out in the presence of a threonine kinase, the threonine kinase is preferably a mitogen-activated protein kinase(MKK), alternatively called stress activated protein kinase (SKK). More particularly, the kinase is MKK7/SKK4.

According to one embodiment of the process of the present invention, an antibody is added preferably at the start of the reaction having a specificity to the bis-phosphorylated sequence, preferably to phosphorylated threonine or serine. During the enzyme reaction any double phosphorylated product formed is bound by the antibody. Then, at the end of the enzyme reaction, a labelled, double phosphorylated ligand is added, either with or without the concomitant addition of a reagent to stop the reaction, to compete with the double phosphorylated protein or peptide for binding to the antibody. This indirect assay principle is based on the fact that if the substrate becomes double phosphorylated by the kinase such as MKK7, it will compete with the labelled, double phosphorylated peptide-antibody complex. This strategy has the advantage of using non-labelled substrates and a fixed antigen-antibody complex that gives the readout.

Usually, the double phosphorylated ligand is labelled by common techniques, using a luminescent or a radioactive tag or by molecules such as a reporter enzyme or an affinity ligand. Preferably, the ligand is labelled by a fluorescent dye. Particularly, the ligand comprises or is composed of the sequence 5-TAMRA-AEEA-Lys-Phe-Met-Met-pThr-Pro-pTyr-Val-Val-Thr-Arg-NH$_2$. (SEQ ID NO:4).

In FIG. 1 the indirect assay principle is illustratively shown. The P1°substrate having the amino acid sequence H-Lys-Phe-Met-Met-Thr-Pro-pTyr-Val-Val-Thr-Arg-NH$_2$ (SEQ ID NO:1) (p means phosporylated) becomes phosphorylated at the threonine residue in the presence of ATP and the MKK7 kinase. This double-phosphorylated peptide (ligand) competes with the labelled TAMRA-P1*° peptide having the sequence 5-TAMRA-AEEA-Lys-Phe-Met-Met-pThr-Pro-pTyr-Val-Val-Thr-Arg-NH$_2$ (SEQ ID NO:4) for binding to the antibody.

In a preferred embodiment, the assay may be conveniently performed as a fluorescence immunoassay, in particular fluorescence polarization (FP) immunoassay. However, other fluorescence techniques such as fluorescence correlation spectroscopy (FCS), fluorescence intensity distribution analysis (FIDA), fluorescence quenching (FQ) or fluorescence resonance energy transfer (FRET) might be applied.

According to the invention a kit for detecting threonine or serine kinase activity is provided. The kit comprises preferably the following components:

1. a threonine or serine kinase such as natural or recombinant enzyme;
2. a substrate as outlined above, e.g. in form of a mono-phosphorylated-peptide or mono-phosphorylated protein;
3. an antibody as outlined above;
4. reaction buffers including e.g. either MnCl$_2$ or MgCl$_2$, and a phosphate donor such as ATP;
5. reaction vials; and
6. protocol It is preferred that the kit includes a substrate and an antibody as defined above and optionally also reaction buffers, vials and protocols. The user of the kit may have the option to choose an appropriate kinase himself. In a further embodiment, the kit might also include a specific threonine or serine kinase.

The kit preferably further comprises a labelled (in particular luminescently labelled) ligand, which ligand comprises a sequence motif —Z—X—Y— or —Y—X—Z— wherein Z=threonine or serine
X=a sequence of preferably between 1 and 1000 amino acids which may be the same or different
Y=tyrosine, threonine or serine This ligand acts as a competitor for performing the assay according to the present invention, said competitor being pre-phosphorylated at the Z and Y positions.

Figure 2:
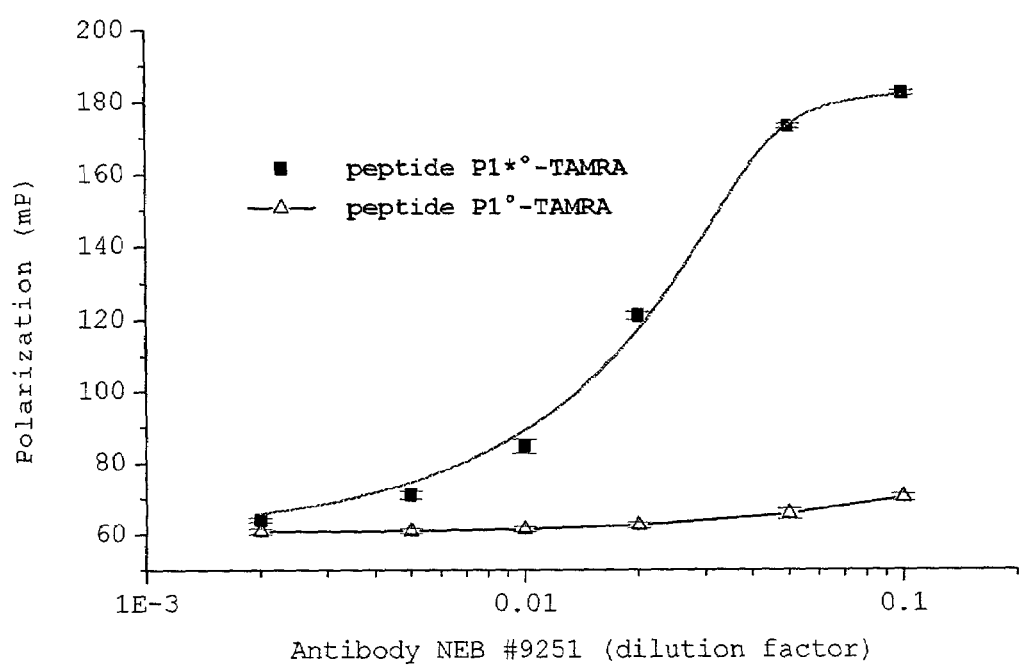
FIG. 2 is a schematic diagram showing the binding of the polyclonal JNK antibody to TAMRA-labelled P1*°-peptide; as a control, no binding is measured for TAMRA-labelled P1°-peptide.

It has been revealed that the commercially available polyclonal anti-phospho-kinase antibodies are particularly useful in the assay of the present invention. As can be seen in FIG. 2 (ref. Example 1), the polyclonal phospho-JNK antibody detects all three isoforms of the JNK proteins only when activated by dual phosphorylation at threonine$_{183}$ and tyrosine$_{185}$. The polarization values dramatically increase when using the double-phosphorylated peptide substrate P1*° in contrast to mono-phosphorylated labelled peptide P1° (sequence see above).

Figure 3:
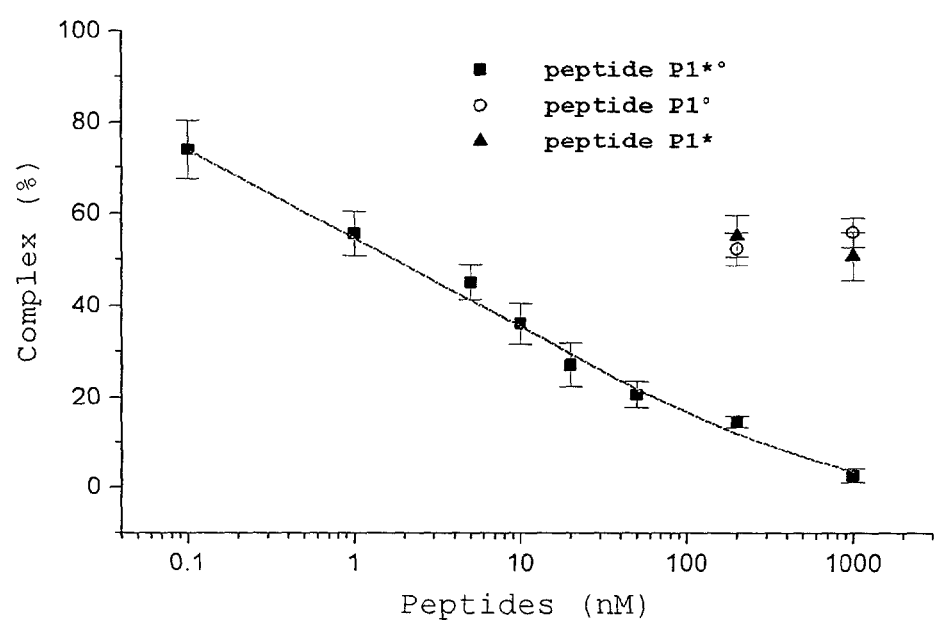
FIG. 3 is a schematic diagram showing the competition of the binding of the polyclonal JNK antibody to the TAMRA-labelled P1*°-peptide using monophosphorylated P1°- and P1*-peptides and double-phosphorylated P1*°-peptide (determination of the IC50 for the P1*°-peptide competitor).

In FIG. 3 (ref. Example 2) the binding of the same polyclonal antibody to TAMRA-labelled peptide P1*° (5 nM) in competition with the peptides P1° (mono-phosphorylated, sequence see above), peptide P1* (mono-phosphorylated having the sequence H-Lys-Phe-Met-Met-pThr-Pro-Tyr-Val-Val-Thr-Arg-NH$_2$) (SEQ ID NO:2) or peptide P1*° (double phosphorylated, sequence see above) is presented. As can be deduced from the complex formation, only bis-phosphorylated peptide P1*° is able to compete effectively with the TAMRA-labelled peptide P1*° for binding to the antibody while the other mono-phosphorylated peptides displace less than 50% of the bound ligand even at high concentrations (up to 1 µM).

Figure 4:
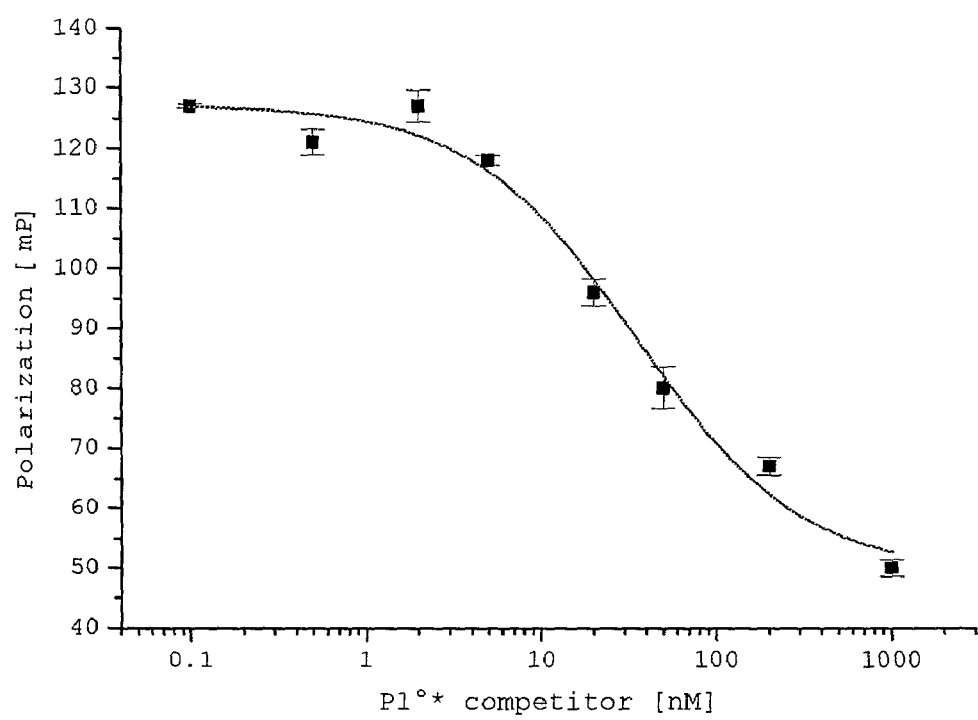
FIG. 4 is a schematic diagram showing the competition of the binding of the polyclonal JNK antibody to the TAMRA-labelled P1*°-peptide in presence of 100 µM P1°-peptide (substrate) using P1*°-peptide (determination of the IC50 for the P1*°-peptide competitor under MKK7 kinase assay conditions).

In FIG. 4 (ref. Example 3) the binding of the same polyclonal antibody to TAMRA-labelled peptide P1*° (5 nM) is displaced by bis-phosphorylated competitor peptide in presence of P1° peptide substrate (100 µM). These conditions reflect the concentration at which P1° peptide is used as a substrate for the MKK7 kinase. As can be seen from the result, the presence of mono-phosphorylated P1° peptide does not reduce the dynamic range of the described kinase assay.

Figure 5:
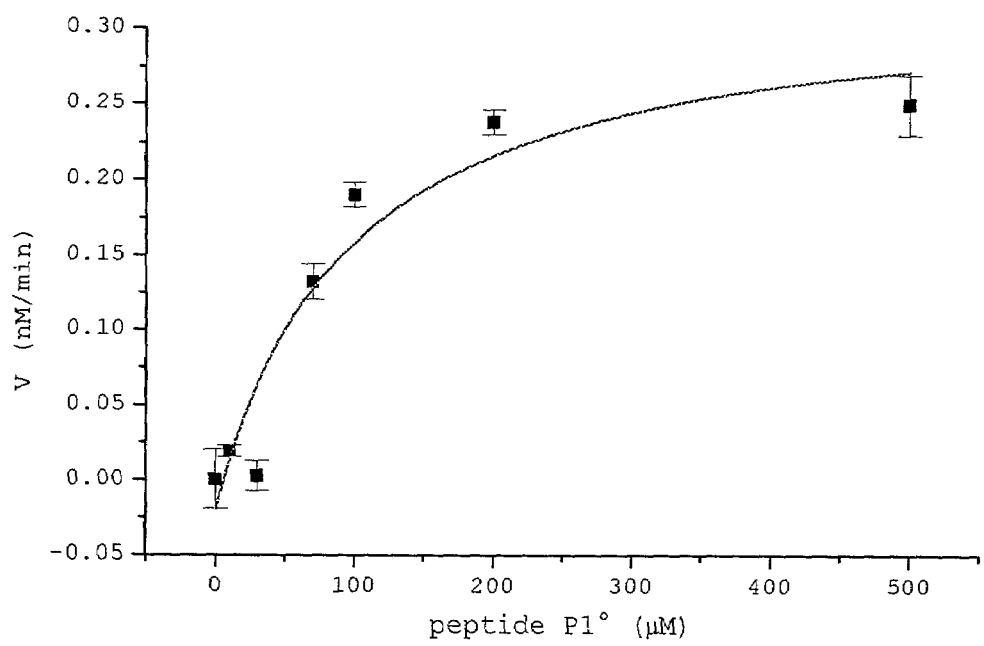
FIG. 5 is a schematic diagram showing the phosphorylation of P1°-peptide substrate by MKK7 kinase at different P1°-peptide concentrations (determination of the Km for P1°-peptide).

In FIG. 5 (ref. Example 4) the rate of phosphorylation of P1° peptide substrate by MKK7 kinase is determined at various P1° peptide concentrations. Efficient phosphorylation of P1° peptide is measured. The formed double-phosphorylated P1*° peptide product can be detected as it competes with the TAMRA-labelled P1*° peptide for the binding to the same polyclonal phospho-JNK antibody. As a results, a drop of the fluorescence polarization is detected which is inversely proportional to MKK7 kinase activity. From the detected signals, the Michaelis-Menten constant (Km), reflecting the half-maximal phosphorylation rate, was determined for P1° peptide.

Figure 6:
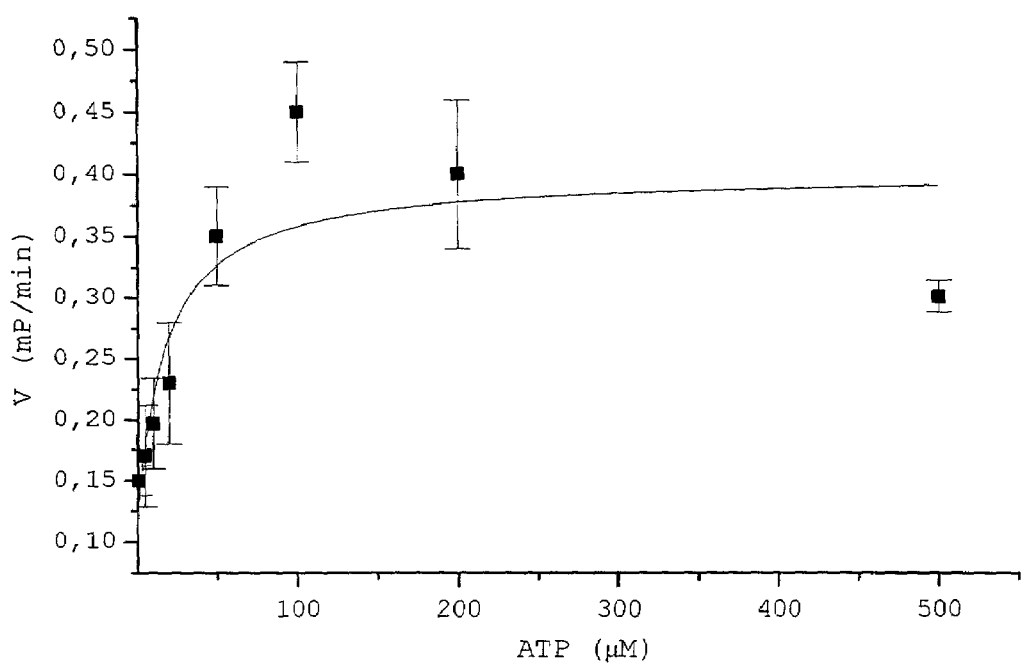
FIG. 6 is a schematic diagram showing the phosphorylation of P1°-peptide substrate by MKK7 kinase at different ATP concentrations (determination of the Km for ATP).

In FIG. 6 (ref. Example 5) the rate of phosphorylation of P1° peptide substrate by MKK7 kinase is determined at different ATP concentrations. Efficient phosphorylation of P1° peptide is dependent on the optimal ATP concentration. The formation of the bis-phosphorylated P1*° peptide product is detected using the same competition assay as described in FIG. 5. From the detected fluorescence polarization signals, the Michaelis-Menten constant (Km), reflecting the half-maximal phosphorylation rate, was determined for ATP.

Figure 7:
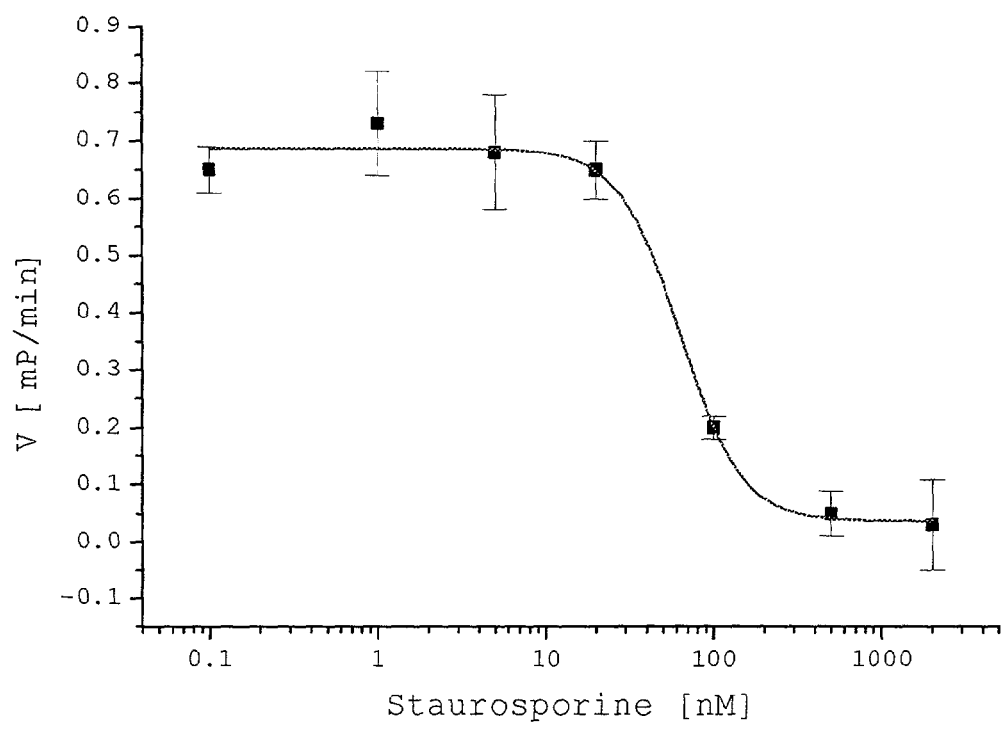
FIG. 7 is a schematic diagram showing the inhibition of the MKK7 kinase-dependent phosphorylation of P1$^{602}$-peptide substrate by Staurosporine (determination of the IC50 for Staurosporine).

In FIG. 7 (ref. Example 6) the inhibition of the phosphorylation of P1° peptide substrate by MKK7 kinase is determined for the kinase inhibitor staurosporine. The inhibition of MKK7 kinase is detected using the same competition assay as described in FIG. 5. As a result, no competition of the TAMRA-labelled P1*° peptide from the same polyclonal phospho-JNK antibody is detected at high Staurosporine concentrations. The half-maximal inhibitory concentration (IC50) was calculated for Staurosporine.

The following examples illustrate the assay of the present invention. The experiments described hereinafter show the feasibility to monitor the phosphorylating activity of serine/threonine kinases in a homogeneous assay format amenable to high throughput screening. The experiments are based on the finding that a modification—phosphorylation at the Y position—of the substrate in spacial proximity to the Z-site of phosphorylation not only enhances the affinity of the phosphorylated product to the detection antibody but also results in a high specificity for the phosphorylated Z position. Besides having the advantage of affinity enhancement of the antibody, the modification of the substrate according to the present invention turns out to have an unexpected positive effect on the kinetics of the kinase reaction as well.

EXAMPLES

Example 1

Measurement of the Binding Affinity (KD) of Antibody NEB #9251:

This polyclonal antibody detects all three isoforms of the SAPK1/JNK proteins only when they are activated by dual phosphorylation at threonine$_{183}$/tyrosine$_{185}$. Binding of poly-clonal phospho-JNK antibody (at a dilution of 1:20) from NEB to TAMRA-labelled P1°- and P1*° peptides (each 5 nM) was measured by fluorescence polarization.

Affinity of polyclonal phospho-JNK antibody for peptide P1*°-TAMRA: $K_D$=2.6 nM The results of this experiment are illustrated in FIG. 2.

Example 2

Determination of IC50 for Peptide P1°:

Competition of NEB antibody-P1*°-TAMRA complex with P1*° peptide was measured by fluorescence correlation spectroscopy: Binding of polyclonal phospho-SAPK1/JNK antibody from NEB (1:20 diluted) to TAMRA-labelled peptide P1*° (5 nM) was competed with non-fluorescent, double-phosphorylated peptide P1*°. Control peptides: mono-phosphorylated P1° and P1*°.

Peptide P1*°: $IC_{50}$=5.0 nM±3.3 nM

The results of this experiment are illustrated in FIG. 3.

Example 3

Determination of IC50 for Peptide P1°(Under MKK7 Enzyme Assay Conditions).

Competition of NEB antibody-P1*°-TAMRA complex with P1*° in presence of P1° substrate peptide (reflecting MKK7 assay conditions) was measured by fluorescence polarization: Binding of polyclonal phospho-JNK antibody from NEB #9251 (at a dilution of 1:20) to TAMRA-labelled peptide P1*° (5 nM), competition with P1*° peptide (0.1, 0.5, 2, 5, 20, 50, 200, 2000 nM) in Hepes buffer, MgCl$_2$ 10 mM, ATP 20 µM, Pluronic 0.1%, P1° substrate peptide 100 µM.

Peptide P1*°: IC$_{50}$=35.1 nM±10.6 nM

The results of this experiment are illustrated in FIG. 4.

Example 4

Determination of Km for Peptide P1°(Read-out: Fluorescence Polarization):

Assay conditions: MKK7 kinase (80 nM), P1° peptide (0, 10, 30, 70, 100, 200, 500 µM), ATP (100 µM), NEB antibody #9251 (1:20) diluted and P1*° peptide-TAMRA (5 nM) at RT (room temperature).

K$_m$=94 nM±59 nM, V$_{max}$=94.6 nM/min±0.03 nM/min

The results of this experiment are illustrated in FIG. 5.

Example 5

Determination of Km for ATP (Read-out: Fluorescence Polarization):

Assay conditions: MKK7 (80 nM), P1° peptide (100 µM), ATP (0, 1, 5, 10, 20, 50, 100, 200, 500 µM), incubation time to 2 h at RT, polyclonal active-JNK antibody from NEB #9251 (1:20 dilution) and P1*° peptide-TAMRA at (5 nM).

K$_m$=17.3 nM±18.1 nM, V$_{max}$=0.28 mP/min±0.07 mP/min

The results of this experiment are illustrated in FIG. 6.

Example 6

Inhibition of MKK7 Activity with Staurosporine (Read-out: Fluorescence Polarization):

Assay conditions: MKK7 (0.3 µM), P1° peptide (100 µM), ATP (10 µM), Staurosporine (0, 0.05, 0.2, 1, 2, 5, 10 µM), polyclonal active-JNK antibody from NEB #9251 (1:20 dilution) and P1*° peptide-TAMRA at (5 nM).

IC$_{50}$=63.3 nM±10.2 nM

The results of this experiment are illustrated in FIG. 7.

Example 7

Fluorescence Polarization measurements of MKK7 activity (time course): In this experiment, the time course has been investigated at P1° substrate concentrations of 100 µM. The reactions were stopped with EDTA.

The following reagents have been used (the compositions of the buffers and specifications of the reagents are explained in more detail later on): Hepes buffer, MgCl$_2$ 10 mM, ATP 20 µM, P1° peptide at 100 µM, NEB antibody # 9251 1:20 dilution, P1*°-TAMRA 5 nM, Pluronic 0.1%, MKK7 at 0, 0.005, 0.02, 0.08, 0.2, 0.5 and 2 µM.

After addition of MKK7, the enzyme reactions were performed in Nunc chambers at RT. The samples were continuously measured at different time points by Fluorescence polarization.

|  |  |  |  |  | 0 h |
|---|---|---|---|---|---|
| Conjugate: P1*°-Tamra |  |  |  |  | 39.7 |
| High: P1*°-Tamra + NEB ab (1:20) |  |  |  |  | 139.1 |
| Low: P1*°-Tamra + NEB ab (1:20) + P1*°200 nM |  |  |  |  | 84.5 |
| 100 µM P1° | 0 h | 0.5 h | 1 h | 1.5 h | 3 h |
| MKK7: 0.0 µM | 134.7 | 139.1 | 139.7 | 140.2 | 144.8 |
| MKK7: 0.005 µM | 131.5 | 137.4 | 136.8 | 136.9 | 138.1 |
| MKK7: 0.02 µM | 135.4 | 140.3 | 140.9 | 139.7 | 140.0 |
| MKK7: 0.08 µM | 133.5 | 137.6 | 135.8 | 128.4 | 115.2 |
| MKK7: 0.2 µM | 135.3 | 132.1 | 121.9 | 113.8 | 104.7 |
| MKK7: 0.5 µM | 135.3 | 125.5 | 115.3 | 108.8 | 106.6 |
| MKK7: 1.0 µM | 135.7 | 119.6 | 112.2 | 105.3 | 108.4 |

Fluorescence Polarization (FP) values are given in mP.

Example 8

Fluorescence Polarization measurements of MKK7 activity (time course): In this experiment the assay conditions have been optimized. The reactions were stopped with EDTA.

Two different assay strategies were investigated: first, the NEB read-out antibody was included in the enzyme reaction (STOP solution: contains only EDTA and P1*°-TAMRA); second, the NEB read-out antibody was included in the STOP solution.

The following reagents have been used (explanations later on): Hepes buffer, MgCl$_2$ (10 mM), ATP (20 µM), P1° peptide (100 µM), polyclonal antibody NEB #9251 (1:20), P1*°-TAMRA (5 nM), Pluronic (0.1%), BSA (0.01%), MKK7 at (0.04, 0.08 and 0.2 µM), EDTA (10 mM) (all final conc.).

The enzyme reactions were performed in Eppendorf reaction tubes at RT. Aliquots of 20 µl were withdrawn from the reactions at different time points and mixed with 10 µl STOP solution. The stopped reactions were incubated at RT for at least 30 min and measured by Fluorescence Polarization.

| Results: |  |  |  |  |  |
|---|---|---|---|---|---|
|  |  |  |  |  | 0 h |
| Conjugate: P1*°-Tamra |  |  |  |  | 33.2 |
| High: P1*°-Tamra + NEB ab (1:20) |  |  |  |  | 145.7 |
| Low: P1*°-Tamra + NEB ab (1:20) + P1°200 nM |  |  |  |  | 71.5 |
|  | 0 h | 0.5 h | 1 h | 1.5 h | 2 h | 3 h |
| NEB ab in reaction |  |  |  |  |  |  |
| MKK7: 0.04 µM | 150.0 | 128.5 | 125.7 | 112.9 | 109.7 | 78.6 |
| MKK7: 0.08 µM | 138.5 | 122.5 | 105.9 | 86.4 | 84.5 | 65.0 |
| MKK7: 0.2 µM | 137.2 | 101.4 | 83.1 | 78.1 | 72.1 | 59.4 |
| NEB ab in STOP sol. |  |  |  |  |  |  |
| MKK7: 0.04 µM | 147.2 | 141.5 | 140.2 | 135.8 | 134.2 | 138.2 |
| MKK7: 0.08 µM | 143.3 | 139.1 | 133.6 | 122.1 | 115.8 | 125.0 |
| MKK7: 0.2 µM | 148.2 | 130.2 | 114.0 | 102.8 | 99.2 | 119.4 |

Fluorescence Polarization (FP) values are given in mP.

Example 9

Fluorescence Polarization measurements of MKK7 activity (time course) in Nanocarrier plates (supplier: EVOTEC BioSystems AG, 1.2 µl volume):

Assay conditions (end conc.):

P1° substrate 100 µM, polyclonal antibody NEB #9251 (1:20), ATP 20 µM, MgCl 10 mM MKK7 enzyme: 0, 25, 50, 75, 100, 200, 350, 500 nM STOP solution: EDTA 10 mM, P1*°-TAMRA (5 nM)

Stock solutions:

P1° substrate 125 µM, NEB ab (1:13.3), ATP 25 µM, MgCl 12.5 mM

MKK7 enzyme: 2500 nM
STOP solution: EDTA 60 mM, P1-TAMRA 30 nM
Solutions 1.–3. in Hepes buffer, Pluronic 0.1%, BSA 0.01%.

It has been revealed that bis-phosphorylated-TAMRA-P1*°-peptide (ligand) is bound by the polyclonal anti-active JNK-antibody, which is called "high" or "positive control".

Bis-phosphorylated peptide P1*° can be used as competitor, resulting in free labelled ligand called "low" or "negative control". This can be seen in the following table 1.

TABLE 1

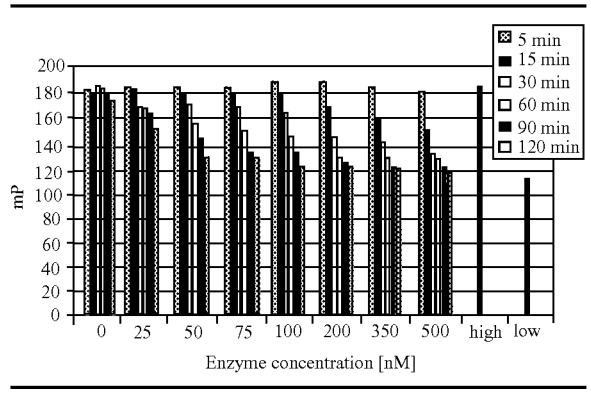

FP values are given in mP. The bars illustrate the time course at different enzyme concentrations. "List of reagents of the MKK7 kinase . . . The stock should be aliquoted in 10 μl aliquots and kept at −20° C." with the following rewritten text:

List of reagents of the MKK7 kinase assay:
List of used JNK1-peptides:
P1°   H-Lys-Phe-Met-Met-Thr-Pro-pTyr-Val-Val-Thr-Arg-NH2 (SEQ ID NO:1)
P1*   H-Lys-Phe-Met-Met-pThr-Pro-Tyr-Val-Val-Thr-Arg-NH2 (SEQ ID NO:2)
P1*°  H-Lys-Phe-Met-Met-pThr-Pro-pTyr-Val-Val-Thr-Arg-NH2 (SEQ ID NO:3)
TAMRA-P1*°   5-TAMRA-AEEA-Lys-Phe-Met-Met-pThr-Pro-pTyr-Val-Val-Thr-Arg-NH2 (SEQ ID NO:4)
Ligand:
TAMRA-P1*°-Peptide:  5-TAMRA-AEEA-Lys-Phe-Met-Met-pThr-Pro-pTyr-Val-Val-Thr-Arg-NH2 (SEQ ID NO:4)
Supplier: EVOTEC BioSystems AG, solid-phase peptide synthesis HK-03-65-P1-13; M=2089 g/mol; MALDI (2092.18)
1 mM stock solution in 100% DMSO
The stock should be aliquoted in 10 μl aliquots and kept at −20° C.
5 nM working solution.
Competitor:
P1*°-Peptide: H-Lys-Phe-Met-Met-pThr-Pro-pTyr-Val-Val-Thr-Arg-NH2 (SEQ ID NO:3)
Supplier: EVOTEC BioSystems AG, solid-phase peptide synthesis HK-03-60-P1-7; M=1532 g/mol; MALDI (1531.88)
10 mM stock solution in 100% DMSO
The stock should be aliquoted in 10 μl aliquots and kept at −20° C.
200 μM working solution.
Substrate: MKK7 kinase substrate
P1°-Peptide: H-Lys-Phe-Met-Met-Thr-Pro-pTyr-Val-Val-Thr-Arg-NH2 (SEQ ID NO:1)
Supplier: EVOTEC BioSystems AG, solid-phase peptide synthesis HK-03-58-HF; M=1451 g/mol; MALDI (1453.57)
10 mM stock solution in 100% DMSO
The stock should be aliquoted in 10 μl aliquots and kept at −20° C.
100 μM working solution.
Enzyme:
MKK7 kinase Supplier: Upstate Biotech cat. no. 14-366, lot no. 19105 and no. 20658.
See enzyme activity specifications on the respective certificate of analysis.
Specific activity: Approximately 20 Units/mg when max. activated.
20 μg of enzyme (9 μM) in 50 μl of 50 mM Tris-HCl, pH 7.5, 150 mM NaCl, 270 mM sucrose, 0.1 mM EGTA, 0.1% 2-mercaptoethanol, 0.03% Brij-35, 1 mM benzamidine, 0.2 mM PMSF.
The stock was kept at −70° C. Freezing and thawing cycles were avoided.
Anti active SAPK1/JNK-specific antibody:
New England Biolabs, U.S.A.: NEB #9251
Anti active JNK polyclonal antibody purified via affinity chromatography (Protein A) from rabbit serum, conc.: 0.02 mg/ml, equiv. 130 nM. Storage buffer: 10 mM Hepes pH 7.5, 150 mM NaCl, 100 μg/ml BSA, 50% glycerol, store at −70° C. The stock should be aliquoted in 10 μl aliquots and kept at −20° C.
Working solution: 1:20 dilution in 1× Assay-Buffer/0.1% Pluronic
Reagents and buffers:
Assay buffer:
10× HEPES-Assay-Buffer pH 7.5
500 mM HEPES
1 mM EGTA
100 mM DTT
62.5 mM NaCl
Dissolve 770 mg DTT (FLUKA cat. no. 43815; MW 154.25 g/mol) [final concentration 100 nmM] in 30 ml of Millipore water, add 625 μl of 5M $NaCl_2$ [final concentration 62.5 mM], 19.02 mg EGTA (Merck cat. No.1.06404; MW 380.35 g/mol) [final concentration 1 mM] and 5.96 g HEPES (FLUKA cat. no. 54457) [final concentration 500 mM] and adjust pH with 1M NaOH to pH 7.5. Top up to 50 ml with Millipore water. The buffer was filtered sterile (0.22 μm) aliquoted to 1.5 ml and was stored at −20° C.
1M $MgCl_2$:
Dissolve 10.2 g $MgCl_2.6H_2O$ (FLUKA cat. no. 63068) in 50 ml of Millipore water. Buffer was filtered (0.42 μm) and can be stored at 4° C. for several months.
1% (w/v) Pluronic F-127
Dissolve 0.5 g Pluronic (Sigma, cat. no. P-2443) in 50 ml of Millipore water. Stir gently to get a clear solution. Solution was filtered (0.42 μm) and can be stored at 4° C. for several months.
1× HEPES-Assay-Buffer/0.1% Pluronic pH 7.5: (15 ml):
50 mM HEPES
0.1 mM EGTA
10 mM DTT
0.1% Pluronic
Add 1.5 ml 1% (w/v) Pluronic F-127 in water and 1.5 ml of 10× HEPES-Assay-Buffer pH 7.5.to 12 ml of Millipore water. Stir the mixture and check the pH value. The mixture could be stored at 4° C. for 1–2 weeks.
0.5M EDTA (50 ml):
Dissolve 9.309 g EDTA (Roche Molecular Biochemicals, cat. no. 808288) in 40 ml of Millipore water and adjust pH to 8–9 with 10M NaOH in order to get a clear solution. Top up to 50 ml with Millipore water. Buffer was filtered (0.42 μm) and can be stored at 4° C. for several months.
10 mM ATP (15 ml):
Dissolve 9.1 mg ATP (Roche Molecular Biochemicals, cat. no. 126888) in 1.5 ml 1× HEPES-Assay-Buffer/0.1% Pluronic pH 7.5. The solution was filtered (0.42 μm) and can be stored at −20° C. for 2 weeks.

DMSO: 100% DMSO

The solvent was purchased from SIGMA (cat. No. P-2650), sterile filtered.

The invention claimed is:

1. An immunoassay for screening modulators of threonine or serine kinase activity comprising:

a) providing a threonine or serine kinase substrate protein or peptide comprising the sequence motif -Z-X—Y or —Y—X-Z- wherein

Z=threonine or serine

X=a sequence of amino acids-in the range of between 1 and 1000 amino acids, which may be the same or different Y=phospho-tyrosine, phospho-threonine or phospho-serine;

b) adding a test compound;

c) incubating the protein or peptide with a phosphate donor and a threonine or serine kinase under conditions and for a sufficient time to permit phosphorylation of the Z position of the kinase substrate peptide or protein, wherein the kinase substrate may be a labeled or unlabeled compound:

d) adding an antibody having a specificity to the kinase substrate peptide or protein which is phosphorylated at the Y and Z positions, wherein the antibody may be a labeled or unlabeled antibody;

e) detecting the threonine or serine kinase activity; and f) comparing the threonine or serine kinase activity in the presence of the test compound with the threonine or serine kinase activity in the absence of the test compound, wherein altered threonine or serine kinase activity, detected by either labeled antibody or labeled kinase substrate, in the presence of the test compound relative to threonine or serine kinase activity in the absence of the test compound indicates a modulator of threonine or serine kinase activity.

2. The immunoassay of claim 1, wherein a threonine or serine kinase inhibitor is indicated by lower threonine or serine kinase activity in the presence of the test compound relative to the threonine or serine kinase activity in the absence of the test compound.

3. The immunoassay according to claim 1, wherein the phosphate donor is ATP, GTP, or a synthetic cosubstrate.

4. The immunoassay according to claim 1, wherein the immunoassay is performed as a direct binding immunoassay.

5. The immunoassay according to claim 4, wherein said peptide or protein further comprises a molecular label.

6. The immunoassay according to claim 4, wherein said antibody further comprises a molecular label.

7. The immunoassay according to claim 5, wherein said label is selected from the group consisting of a luminescent tag, a radioactive marker, a reporter enzyme, and an affinity ligand.

8. The immunoassay according to claim 1, wherein the immunoassay is performed as an indirect binding immunoassay.

9. The immunoassay according to claim 8 further comprising:

g) adding a competitor protein or competitor peptide comprising the sequence motif -Z'-X'—Y'— or —Y'—X'-Z- wherein

Z'=phospho-threonine or phospho-serine

X'=a sequence of amino acids, preferably between 1 and 1000 amino acids, which may be the same or different Y'=phospho-tyrosine, phospho-threonine or phospho-serine.

10. The immunoassay according to claim 9, wherein the competitor protein or competitor peptide further comprises a label selected from the group consisting of a luminescent tag, a radioactive marker, a reporter enzyme, and an affinity tag.

11. The immunoassay according to claim 10, wherein the competitor protein or competitor peptide comprises the amino acid sequence of SEQ ID NO:3 such that said sequence motif is

—Y'—X'-Z'- wherein
Y' is phosphorylated Tyr at position 5 of SEQ ID NO:3,
X' is Pro at position 6 of SEQ ID NO:3, and
Z' is phosphorylated Thr at position 7 of SEQ ID NO:3.

12. The immunoassay according to claim 1, wherein said e) detecting threonine or serine kinase activity is achieved by fluorescence detection, fluorescence polarization analysis, fluorescence correlation spectroscopy, fluorescence resonance energy transfer analysis, or fluorescence intensity distribution analysis.

13. The immunoassay according to claim 1, wherein the threonine or serine kinase is a threonine kinase.

14. A The immunoassay according to claim 1, wherein the substrate protein or substrate peptide comprises the amino acid sequence of SEQ ID NO:2 such that said sequence motif is

—Y—X-Z- wherein
Y is phosphorylated Tyr at position 5 of SEQ ID NO:2,
X is Pro at position 6 of SEQ ID NO:2, and
Z is Thr at position 7 of SEQ ID NO:2.

15. An immunoassay for screening modulators of threonine or serine kinase activity comprising:
a) providing a threonine or serine kinase substrate protein or peptide comprising the sequence motif -Z-X—Y— or —Y—X-Z- wherein
Z=threonine or serine
X=a sequence of amino acids in the range of between 1 and 1000 amino acids, which may be the same or different
Y=phospho-tyrosine, phospho-threonine or phospho-serine;
b) adding a test compound;
c) incubating the protein or peptide with a phosphate donor and a threonine or senile kinase under conditions and for a sufficient time to permit phosphorylation of the Z position of the kinase substrate protein or peptide;
d) adding an antibody having a specificity to the kinase substrate protein or peptide which is phosphorylated at the Y and Z position;
e) adding a competitor protein or competitor peptide comprising the sequence motif -Z'-X'—Y'— or —Y'—X'-Z- wherein
Z'=phospho-threonine or phospho-serine
X'=a sequence of amino acids in the range of between 1 and 1000 amino acids, which may be the same or different
Y'=phospho-tyrosine, phospho-threonine or phospho-serine, and wherein the competitor protein or competitor peptide is labelled;
f) detecting the threonine or serine kinase activity; and
g) comparing the threonine or serine kinase activity in the presence of the test compound with the threonine or serine kinase activity in the absence of the test compound,
wherein altered threonine or serine kinase activity, detected by labelled competitor protein or competitor peptide, in the presence of the test compound relative to threonine or serine kinase activity in the absence of the test compound indicates a modulator of threonine or serine kinase activity.

16. The immunoassay according to claim 15, wherein a threonine or serine kinase inhibitor is indicated by lower threonine or serine kinase activity in the presence of the test compound relative to the threonine or serine kinase activity in the absence of the test compound.

17. The immunoassay according to claim 15, wherein the phosphate donor is ATP, GTP, or a synthetic cosubstrate.

18. The immunoassay according to claim 15, wherein a label of the competitor protein or competitor peptide is selected from the group consisting of a luminescent tag, a radioactive marker, a reporter enzyme, and an affinity ligand.

19. The immunoassay according to claim 18, wherein the competitor protein or competitor peptide comprises the amino acid sequence of SEQ ID NO:2 such that said sequence motif is —Y'—X'-Z'-
wherein
Y' is phosphorylated Tyr at position 5 of SEQ ID NO:2,
X' is Pro at position 6 of SEQ ID NO:2, and
Z' is phosphorylated Thr at position 7 of SEQ ID NO:2.

20. The immunoassay according to claim 18, wherein the competitor protein or competitor peptide comprises the amino acid sequence of SEQ ID NO:3 such that sequence motif is —Y'—X'-Z'-
wherein
Y' is phosphorylated Tyr at position 5 of SEQ ID NO:3,
X' is Pro at position 6 of SEQ ID NO:3, and
Z' is phosphorylated Thr at position 7 of SEQ ID NO:3.

21. The immunoassay according to claim 15, wherein said f) detecting threonine or serine kinase activity is achieved by fluorescence detection, fluorescence polarization analysis, fluorescence correlation analysis, fluorescence resonance energy transfer analysis, or fluorescence intensity distribution analysis.

22. The immunoassay according to claim 15, wherein the threonine or serine kinase is a threonine kinase.

23. The immunoassay according to claim 15, wherein the kinase substrate protein or peptide comprises the amino acid sequence of SEQ ID NO:2 such that said sequence motif is
—Y—X-Z-
wherein
Y is phosphorylated Tyr at position 5 of SEQ ID NO:2,
X is Pro at position 6 of SEQ ID NO:2, and
Z is Thr at position 7 of SEQ ID NO:2.

24. The immunoassay according to claim 15, wherein the kinase substrate protein or peptide comprises the amino acid sequence of SEQ ID NO:3 such that said sequence motif is
—Y—X-Z-
wherein
Y is phosphorylated Tyr at position 5 of SEQ ID NO:3,
X is Pro at position 6 of SEQ ID NO:3, and
Z is Thr at position 7 of SEQ ID NO:3.

* * * * *

SEQUENCE LISTING

```
<160> NUMBER OF SEQ ID NOS: 5

<210> SEQ ID NO 1
<211> LENGTH: 11
<212> TYPE: PRT
<213> ORGANISM: Artificial Sequence
<220> FEATURE:
<221> NAME/KEY: PHOSPHORYLATION
<222> LOCATION: 7
<223> OTHER INFORMATION: pTyr
<220> FEATURE:
<223> OTHER INFORMATION: peptide based on JNK1/2/3

<400> SEQUENCE: 1

Lys Phe Met Met Thr Pro Tyr Val Val Thr Arg
1               5                   10

<210> SEQ ID NO 2
<211> LENGTH: 11
<212> TYPE: PRT
<213> ORGANISM: Artificial Sequence
<220> FEATURE:
<221> NAME/KEY: PHOSPHORYLATION
<222> LOCATION: 5
<223> OTHER INFORMATION: pThr
<220> FEATURE:
<223> OTHER INFORMATION: peptide based on JNK1/2/3

<400> SEQUENCE: 2

Lys Phe Met Met Thr Pro Tyr Val Val Thr Arg
1               5                   10

<210> SEQ ID NO 3
<211> LENGTH: 11
<212> TYPE: PRT
<213> ORGANISM: Artificial Sequence
<220> FEATURE:
<221> NAME/KEY: PHOSPHORYLATION
<222> LOCATION: 5
<223> OTHER INFORMATION: pThr
<221> NAME/KEY: PHOSPHORYLATION
<222> LOCATION: 7
<223> OTHER INFORMATION: pTyr
<220> FEATURE:
<223> OTHER INFORMATION: peptide based on JNK1/2/3

<400> SEQUENCE: 3

Lys Phe Met Met Thr Pro Tyr Val Val Thr Arg
1               5                   10

<210> SEQ ID NO 4
<211> LENGTH: 11
<212> TYPE: PRT
<213> ORGANISM: Artificial Sequence
<220> FEATURE:
<221> NAME/KEY: PHOSPHORYLATION
<222> LOCATION: 5
<223> OTHER INFORMATION: pThr
<220> FEATURE:
<221> NAME/KEY: VARIANT
<222> LOCATION: (1)...(0)
```

-continued

```
<223> OTHER INFORMATION: Fluorescent tag (TAMRA) and linker (AEEA)
<221> NAME/KEY: PHOSPHORYLATION
<222> LOCATION: 7
<223> OTHER INFORMATION: pTyr
<220> FEATURE:
<223> OTHER INFORMATION: Ligand

<400> SEQUENCE: 4

Lys Phe Met Met Thr Pro Tyr Val Val Thr Arg
 1               5                  10

<210> SEQ ID NO 5
<211> LENGTH: 11
<212> TYPE: PRT
<213> ORGANISM: Artificial Sequence
<220> FEATURE:
<221> NAME/KEY: PHOSPHORYLATION
<222> LOCATION: 5
<223> OTHER INFORMATION: pThr
<221> NAME/KEY: VARIANT
<222> LOCATION: (1)...(0)
<223> OTHER INFORMATION: Fluorescent tag (TAMRA) and linker (Ahx)
<220> FEATURE:
<221> NAME/KEY: PHOSPHORYLATION
<222> LOCATION: 7
<223> OTHER INFORMATION: Variant
<220> FEATURE:
<223> OTHER INFORMATION: pTyr

<400> SEQUENCE: 5

Lys Phe Met Met Thr Pro Tyr Val Val Thr Arg
 1               5                  10
```